(12) United States Patent
McGaffigan et al.

(10) Patent No.: US 6,193,714 B1
(45) Date of Patent: Feb. 27, 2001

(54) MEDICAL PROBE DEVICE WITH TRANSPARENT DISTAL EXTREMITY

(75) Inventors: Thomas H. McGaffigan; Jack A. McCullough, both of Saratoga; Christopher S. Jones, Palo Alto; Bryan C. Depetrillo, San Jose, all of CA (US)

(73) Assignee: Vidamed, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/255,361

(22) Filed: Feb. 23, 1999

Related U.S. Application Data

(63) Continuation of application No. 08/835,956, filed on Apr. 11, 1997, now Pat. No. 5,873,877.

(51) Int. Cl.[7] ............................................... A61B 18/18
(52) U.S. Cl. .............................. 606/41; 606/45; 606/49; 607/101
(58) Field of Search ................................. 606/41, 42, 45, 606/46–50; 607/101–102; 600/171, 175–176

(56) References Cited

U.S. PATENT DOCUMENTS

| 2,008,526 | 7/1935 | Wappler et al. . |
| 2,038,393 | 4/1936 | Wappler . |
| 4,016,886 | 4/1977 | Doss et al. . |
| 4,474,174 | 10/1984 | Petruzzi . |
| 4,524,770 | 6/1985 | Orandi . |
| 4,950,267 | 8/1990 | Ishihara et al. . |
| 5,366,490 | 11/1994 | Edwards et al. . |
| 5,370,675 | 12/1994 | Edwards et al. . |
| 5,409,483 | 4/1995 | Campbell et al. . |
| 5,411,016 | 5/1995 | Kume et al. . |
| 5,435,805 | 7/1995 | Edwards et al. . |
| 5,607,394 | 3/1997 | Andersen et al. . |
| 5,624,399 | 4/1997 | Ackerman . |

FOREIGN PATENT DOCUMENTS

WO 96/22739  8/1996  (WO) .

OTHER PUBLICATIONS

Greenwald Surgical Company, Inc., "Orandi Resectoscope Injection Needle for Injection of Local Anesthetics," (Undated) Sheet No. P000121.

(List continued on next page.)

Primary Examiner—Linda C. M. Dvorak
Assistant Examiner—Roy Gibson
(74) Attorney, Agent, or Firm—Flehr Hohbach Test Albritton & Herbert LLP (57) ABSTRACT

A medical probe device for introduction by way of a natural body opening into a tubular internal anatomical part of the body includes an elongate member having proximal and distal extremities and a passageway extending from the proximal extremity to the distal extremity along a longitudinal axis, a transparent guide piece mounted on the distal extremity of the elongate member, the transparent guide piece having proximal and distal extremities and a bore therein defining a guide piece lumen extending from the proximal extremity of the guide piece distally at least part way to the distal extremity of the guide piece, the guide piece lumen being in communication with the passageway in the elongate member, an optical viewing element movable within the passageway of the elongate member and having a distal extremity movable within the guide piece lumen, a handle mechanism mounted on the proximal extremity of the elongate member, and a further mechanism carried by the handle for mounting the distal extremity of the optical viewing element within the guide piece lumen and for moving the distal extremity of the optical viewing element in a longitudinal direction within the guide piece lumen between a distal position to permit viewing forward of the distal extremity of the guide piece within the body and a proximal position to permit viewing lateral to at least the distal extremity of the guide piece.

8 Claims, 3 Drawing Sheets

OTHER PUBLICATIONS

E.F. Nation, M.D., "Evolution of Knife–Punch Resectoscope," (Apr. 1976) Urology, vol. VII, No. 4, pp. 417–427.

R. Gutierrez, "Transurethral Treatment of Bladder Neck Obstructions: Endoscopic Prostatic Resection," (Apr. 1933) History of Urology, vol. II, Chapter V, pp. 137–186.

C.W. Ogden, Heat and the Prostate from Electrolysis to Microwaves: Lessons from an Historical Perspective, (Undated) Abstract, 2 sheets, p. 366.

Graversen, et al., "Transurethral incisions of the prostate under local anaesthesia in high–risk patients: a pilot study," (1987) Abstract, HealthGate Home Page, p. P000115.

Miller, et al., "Integrated cystoscope: first rigid multipurpose operating cystoscope for local anesthetic endoscopy," (1989) Abstract, HealthGate Home Page, p. P000116.

Orandi, "Urological endoscopic surgery under local anesthesia: a cost–reducing idea," (1984) Abstract, Healthgate Home Page, p. P000117.

Orandi, "Transurethral resection versus transurethral incision of the prostate," (1990) Abstract, HealthGate Home Page, p. P000118.

H. LeVeen, "Method for treating benign and malignant tumors utilizing radio frequency," (Nov. 16, 1976) Abstract, USPTO.GOV, U.S. Pat. No. 3,991,770, pp. P000119–P000120.

R. Auhll, "The Use of the Resectoscope in Gynecology," (Oct. 1990) Biomedical Business International, pp.91–99.

L. Geddes, "A Short History of the Electrical Stimulation of Excitable Tissue Including Electrotherapeutic Applications," (1984) A Supplement to The Physiologist, vol. 27, No. 1, pp. P000066–P000071.

W. Moseley, M.D., "The History of Treatment of BPH Including Current Treatment Alternatives," (Undated) pp. P000187–P000190.

D. Paulson, M.D., "Diseases of the Prostate," (1989) Clinical Symposia, vol. 41, No. 2., pp. P000191–P000195.

T. Kirwin, "The Treatment of Prostatic Hypertrophy by a New 'Shrinkage' Method," (Aug. 1934) J. Urology, pp. 481–494.

MEDICAL PROBE DEVICE WITH TRANSPARENT DISTAL EXTREMITY

This is a continuation of application Ser. No. 08/835,956 filed Apr. 11, 1997, now U.S. Pat. No. 5,873,877.

BACKGROUND

This invention relates generally to elongate medical devices insertable into the body, which are provided with optical viewing apparatus by which a remote site within the body near the distal extremity of the device can be seen from outside the body. Particularly, the invention relates to medical devices insertable into the body by way of a natural body opening, which are provided with optical viewing apparatus and with means, situated near the distal extremity and manipulable from the proximal extremity, for treatment of an internal organ. Such devices include for example transurethral catheter devices for treatment of the prostate.

Conventionally the distal extremity of such a device is introduced into the body and is maneuvered remotely, by manipulation of controls outside the body, to the site within the body that is to be observed and treated. Optical viewing apparatus in such devices typically provides for illumination of part of the region near (typically forward of) the distal extremity, and for conducting an image from the distal extremity to the proximal extremity, where the operator can view it.

Transurethral needle ablation devices having optical viewing capability and designed for treating the tissue of the prostate are described for example in U.S. Pat. Nos. 5,370,675; 5,366,490; and 5,435,805, and International Patent Publication No. WO 96/22739. The optical viewing apparatus in these devices facilitates positioning the distal extremity of the device at the appropriate site within the urethra, by illuminating the interior of the urethra and providing the operator with an image of the urethra wall as the distal extremity of the device is advanced within it toward the treatment site.

Many such procedures entail application of high-frequency electrical current, microwave energy, radio frequency energy, acoustical energy or laser energy to destroy cells in a target tissue. Significant damage to adjacent or surrounding tissues can result from application of the treatment if the treatment means is not precisely positioned before the ablating energy is applied. In a transurethral needle ablation procedure for treatment of the prostate, for example, when the needle electrode is pressed against the urethral wall the tip of the needle may fail to puncture the urethral wall, so that even when the needle is fully deployed it has not crossed into the prostate tissue. Application of electrical energy under these circumstances can result in severe traumna to the urethra.

Accordingly, in some disclosed devices, the optical viewing apparatus is additionally intended to address both a need to observe the progress of the distal extremity of the device to the treatment site, and a need to be able to view the treatment means while the treatment is in progress.

For example, U.S. Pat. No. 5,435,805 is directed to a device (such as a device for treatment of benign prostate hypertroplhy) having optical viewing capability for precise placement of the device which delivers the therapeutic energy into targeted tissues while minimizing effects on surrounding tissue. Particularly, U.S. Pat. No. 5,435,805 discloses a medical probe device having a stylet guide housing with at least one stylet port and means for directing a flexible stylet sideways out through the port into a target tissue, and a fiber optic viewing assembly, which has a viewing field extending forwardly and sidewardly of the guide housing to permit viewing of the stylet as it is deployed sideways from the distal extremity of the guide housing. To provide an unobstructed view of the emerging stylet, in some embodiments a portion of the material of the guide housing is removed to form a transverse depression behind the stylet port. However, the urethral wall is flabby, and tends to collapse into the depression, obscuring the view forward. In other embodiments the guide housing is provided with a window; but such an arrangement is difficult to manufacture and provides only limited visibility.

SUMMARY OF THE INVENTION

We have discovered that medical probe devices can be made with a capability for excellent viewing both during placement of the distal extremity of the device at the treatment site and during the progress of the treatment, by providing the distal extremity of the device with a transparent guide piece having a longitudinal bore within which the tip of an optical viewing element can be positioned. In a more forward position the visual field permits observation in a forward direction, particularly useful during placement of the device, as the distal extremity is directed toward the treatment site. In a more rearward position the visual field includes an image of a distal portion of the guide part, permitting observation of a distal portion of the guide piece and of its surroundings. The guide piece can additionally be provided with means for guided deployment of a treatment element (such as a stylet for application of radio frequency electrical energy, for example), and the optical viewing element can be positioned within the longitudinal bore in the transparent guide piece such that progress of deployment of the treatment element is within the visual field of the optical viewing element. Proper deployment of the treatment element is thus assured by direct observation.

In one general aspect, the invention features a medical probe device for introduction by way of a natural body opening into a tubular internal anatomical part of the body, including an elongate member having proximal and distal extremities and a passageway extending from the proximal extremity to the distal extremity along a longitudinal axis, a transparent guide piece mounted on the distal extremity of the elongate member, handle means mounted on the proximal extremity of the elongate member, and an optical viewing element movable within the passageway in the elongate member. The transparent guide piece has a bore therein defining a guide piece lumen in communication with the passageway in the elongate member and extending from the proximal extremity of the guide piece distally at least part way to the distal extremity of the guide piece. The optical viewing element has a distal extremity movable within the guide piece lumen, and the handle means carries means for mounting the distal extremity of the optical viewing element within the guide piece lumen and for moving the distal extremity of the optical viewing element in a longitudinal direction within the guide piece lumen between distal and proximal positions. The distal position provides a first visual field permitting viewing in a direction distal to the distal extremity of the guide piece, and the proximal position provides a second visual field permitting viewing in a direction lateral to at least the distal extremity of the guide piece In some embodiments the guide piece additionally includes a stylet guiding channel having an opening on a surface of the guide piece, and the device additionally includes a stylet that is slidably movable in the stylet guiding channel. The handle means carries means for mounting the stylet within the stylet guiding channel and for slidably moving the stylet within the stylet guiding channel through the opening. The stylet guiding channel directs the stylet at an angle to the longitudinal axis of the elongate member as the stylet is slidably moved outward through the stylet guiding channel opening, and the distal extremity of the stylet is within the second visual field as the stylet emerges through the opening In preferred embodiments the material of which the transparent guide piece is made has a refractive index in the range about 1.3 to about 1.7 and a luminous transmittance at least about 80% as determined using ASTM D 1003 procedures in a 0.3 mm thick specimen of the material. In some embodiments the transparent guide piece is made of transparent polymer material, which may be one or a combination of a polymer such as a polymethylmethacrylate, cellulose acetate, a polycarbonate, a polyurethane, or a polyethyleneterephthalate; or a glass.

In some embodiments the device additionally includes within the stylet guiding channel a guide tube within the lumen of which the stylet is slidably movable. Usually the guide tube is made of a material comprising metal, such as stainless steel. Usually, to reduce unwanted glare resulting from reflection from the inner surface of the stylet guiding channel or from the outer surface of the guide tube, these surfaces have a matte finish, which may include a conversion coating such as a black oxide coating.

We have further discovered that, employing a transparent guide piece at the distal extremity of the device and a suitably adapted optical viewing element, the operator can be provided with a split image showing simultaneously a view (for example in a lower portion of a circular image) in a forward direction and a view (for example in an upper portion of a circular image) in a lateral direction.

Accordingly, in a further aspect, the invention features a medical probe device for introduction by way of a natural body opening into a tubular internal anatomical part of the body, including an elongate member having image-splitting means at its distal extremity, usually including a planar surface inclined with respect to the optical axis of the optical viewing element.

In a further general aspect, the invention features a medical probe device for treatment of the prostate of a human male, the device including an elongate member having proximal and distal extremities and a passageway extending from the proximal to the distal extremity along a longitudinal axis, with handle means mounted on the proximal extremity and a transparent guide piece mounted on the distal extremity. The transparent guide piece has a bore which defines a guide piece lumen that is in communication with the passageway in the elongate member, extending from the proximal extremity of the guide piece distally at least part way to the distal extremity of the guide piece. The guide piece includes a stylet guiding channel that is in communication with the passageway in the elongate member, and that opens on a surface of the guide piece. The device additionally includes a stylet, slidably movable in the stylet guiding channel, including a radio frequency needle electrode with a sharpened tip and a layer of insulating material coaxially disposed on the radio frequency needle electrode so that a portion of the radio frequency needle electrode is exposed. The handle means includes means for mounting the stylet within the stylet guiding channel and for slidably moving the stylet within the stylet guiding channel through the opening. The stylet guiding channel directs the stylet at an angle to the longitudinal axis of the elongate member as the stylet is slidably moved outward through the stylet guiding channel opening. And the device additionally includes an optical viewing element that is movable within the passageway of the elongate member and that has a distal extremity movable within the guide piece lumen. The handle means includes means for mounting the distal extremity of the optical viewing element within the guide piece lumen and for moving the distal extremity of the optical viewing element in a longitudinal direction within the guide piece lumen between a distal position and a proximal position. The distal position provides a first visual field permitting viewing in a direction distal to the distal extremity of the guide piece and the proximal position provides a second visual field permitting viewing in a direction lateral to at least the distal extremity of the guide piece, and the distal extremity of the stylet is within tile second visual field as the stylet emerges through the opening.

In some embodiments the device additionally includes means cooperative with the handle means and with the means for mounting the distal extremity of the optical viewing element within the guide piece lumen, for reversibly locking the distal extremity of the optical viewing element in each of the distal and the proximal positions. Usually, the locking means includes a cam cooperative with a slot.

Additional features and advantages of the invention will be apparent from the following description in which the preferred embodiments are set forth in detail in conjunction with the accompanying drawings, and from the claims.

DETAILED DESCRIPTION

The invention is here described in detail with specific reference to embodiments of transurethral medical probe devices useful in treatment of the prostate. It will be appreciated that the invention is suitably useful in connection with other devices, insertable into the body, which may be provided with optical viewing apparatus and which are provided with means manipulable from outside the body for observing and treating a site within the body.

All publications cited herein, including patents, and all patent applications cited herein are hereby incorporated by reference in their entirety.

Figure 1:
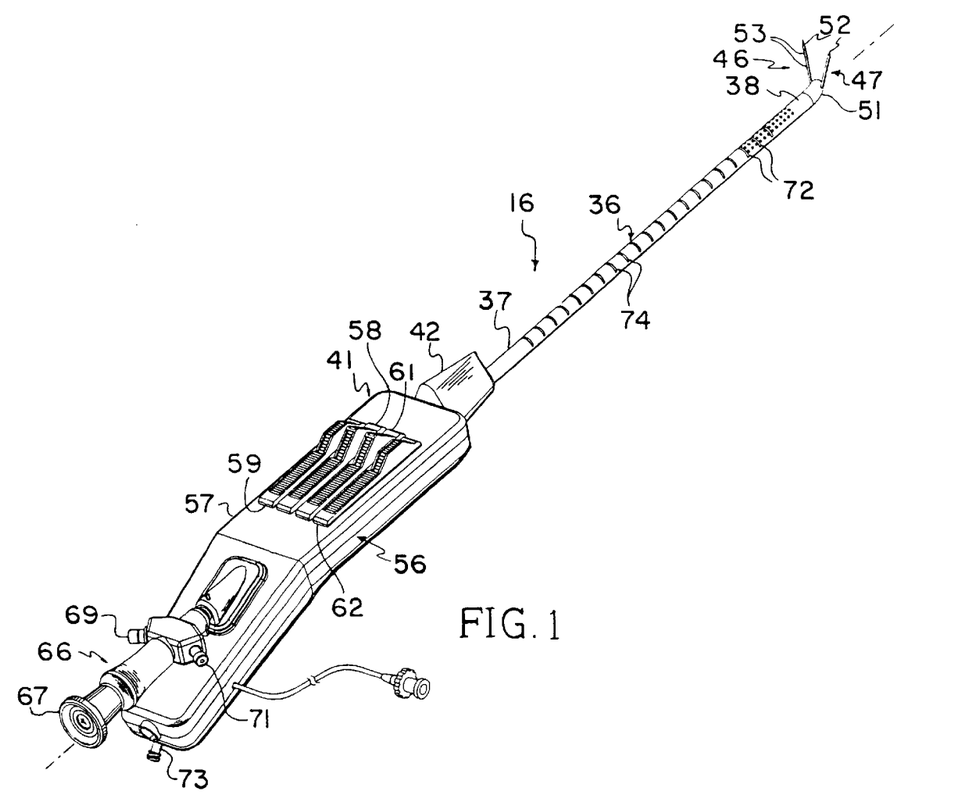
FIG. 1 is a sketch in a perspective view of an embodiment of a medical probe device of the invention.

With reference now to FIG. 1, there is shown generally at 16 an exemplary embodiment of a probe according to the invention. Such probes are described, for example, in copending U.S. patent application Ser. No. 08/833,982 filed Apr. 11, 1997, and also in copending U.S. patent application Ser. No. 29/069,167 filed Apr. 11, 1997, and also in copending U.S. patent application Ser. No. 08/833984 filed Apr. 11, 1997, and also in copending U.S. patent application Ser. No. 08/377,600, filed Jan. 25, 1955. As described therein, probe 16 consists of a rigid elongate sheath 36 formed of a suitable material such as stainless steel. It is of a suitable size as for example 23 French and has proximal and distal extremities 37 and 38 and a length approximately 11". The proximal extremity 37 of the sheath 36 is rotatably mounted on a handle 41 which is sized so as adapted to be grasped by an adult human hand. A knob 42 is provided on the proximal extremity 37 and is adapted to be grasped by a finger of the hand as for example the thumb to permit rotational movement of the sheath 36 for a purpose hereinafter described. The sheath 36 carries at least one and preferably first and second needle electrode assemblies 46 and 47 which are slidably mounted in the sheath 36 and which are directed through a transparent or clear rounded or bullet-shaped tip 51 in off axis or sidewise projecting positions at divergent angles with respect to each other as for example an angle ranging from 30–60°. Each of the first and second needle electrode assemblies 46 and 47 consists of a conductive metal electrode 52 formed of a suitable material such as Nitinol and which is provided with a sharpened tip. A sleeve 53 formed of an insulating material is provided on each electrode and is slidably mounted with respect thereto so that predetermined lengths of the needle electrodes can be exposed in performing the radio frequency ablation as hereinafter described.

The handle 41 is formed of a two part case or housing 56 formed of a suitable material such as plastic. The housing 56 is provided with a flat upper surface 57 on which sliders 58 and 59 are mounted which are provided for controlling respectively the motion of the electrode 52 and the sleeve 53 of the first needle assembly 46 and sliders 61 and 62 are provided for controlling respectively the electrode 52 and the sleeve 53 of the second needle electrode assembly 47. The sliders 58, 59 and 61 and 62 are adapted to be grasped by the thumb of the hand while the handle 41 is being held in the hand.

An optical viewing device 66 is slidably mounted in the handle 41 and is movable between the first and second positions and in the first position extending through the sheath 36 and through the transparent rounded tip 51 so that viewing of the region distally of the tip can be explored and a second position in which it is retracted into the sheath but beings adjacent the transparent rounded tip 51 so that deployment of the first and second needle assembles 46 and 47 can be observed.

The optical viewing device 66 includes an eye piece 67 through which viewing can occur. It also includes a fitting 68 which is provided with an adapter 69 which is adapted to be connected to a suitable source of light (not shown). It is also provided with another fitting 71 through which an irrigation liquid as for example a saline solution can be introduced. The liquid introduced passes through the sheath 36 and exits through the tip 51 into the tissue to be ablated to provide a clear field of view for viewing through the optical viewing device 66. The liquid introduced can be aspirated through a plurality of holes 72 provided in the sheath 36 and passing through the sheath and the housing 56 where it can be aspirated through an aspiration port 73 connected to a suitable source of vacuum. Spaced apart marks 74 are provided on the sheath to indicate to the physician performing the ablation procedure the length of deployment of the probe 16 into the urethra as hereinafter described.

Figure 2:
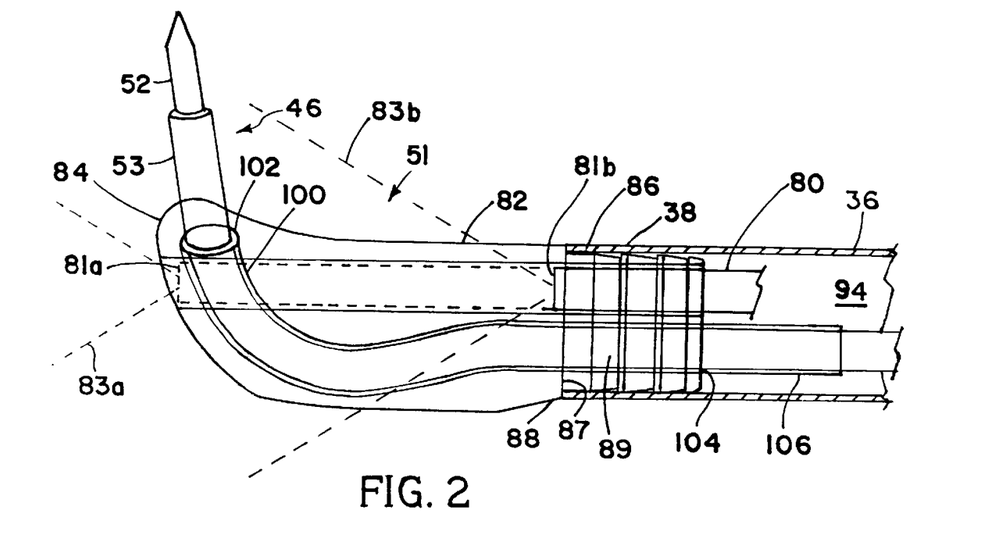
FIG. 2 is a sketch in a side elevational view of the distal extremity of the embodiment of FIG. 1.

FIG. 2 shows in further detail the distal extremity 38 of elongate sheath 36, together with transparent guide piece 51 and needle electrode assembly 46 consisting of conductive electrode 52 and insulating sleeve 53. Transparent guide piece 51 has distal and proximal extremities 84, 86. Proximal extremity 86 includes a shoulder 87 which abuts the end 88 of the distal extremity 88 of elongate sheath 36 when a press-fit portion 89 of guide piece proximal extremity 86 is inserted thereto.

Needle electrode assembly 46 is shown in FIG. 2 partially deployed as if it were entering(g the tissue to be treated (not shown in the FIGS.). The distal extremity 80 of optical viewing device 66 is shown in FIG. 2 in a first more distal position (broken lines, 81a), providing a first visual field 83a permitting viewing in a direction distal to the distal extremity 84 of the transparent guide piece 51, and in second a more proximal position 81b providing a second visual field 83b permitting viewing in a direction lateral to at least the distal extremity 84 of the guide piece, and including the electrode assembly 46.

Figure 3:
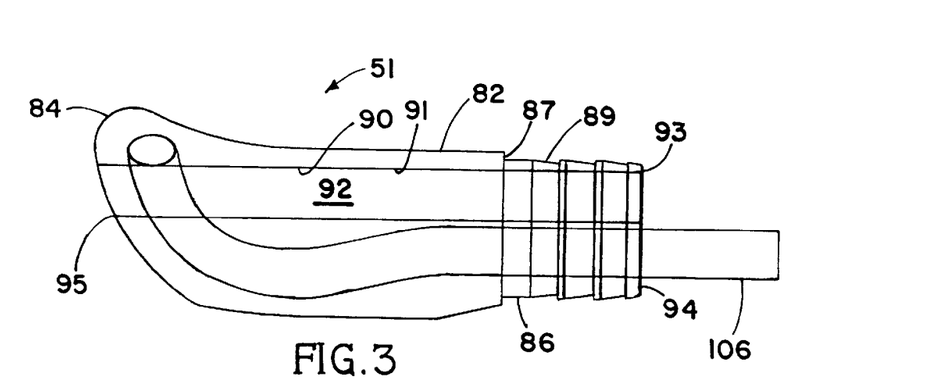
FIG. 3 is a sketch in a side elevational view as in FIG. 2 of a transparent guide piece of the invention.
Figure 4:
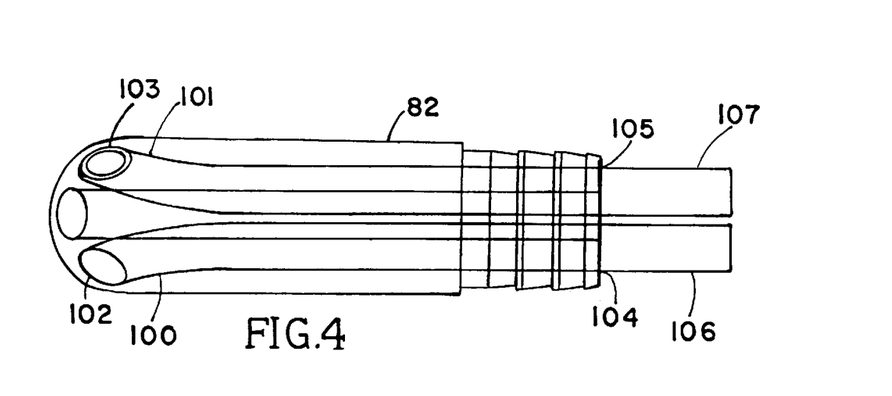
FIG. 4 is a sketch in a plan view of the transparent guide piece of FIG. 3.

Certain features of the transparent guide piece 51 are more clearly seen in FIGS. 3 and 4. Transparent guide piece 51 has a body 82, formed of a transparent material, having a bullet shape, with proximal and distal extremities 84, 86. Transparent guide piece body 82 has a longitudinal bore 90 describing a lumen 92 which has an opening 93 at the proximal end 95 of the guide piece body 82. Lumen 92 communicates with a passageway 94 that runs the length of the elongate sheath 36, and is suitably dimensioned to receive the distal extremity 80 of optical viewing device 66. Bore 90 passes distally at least part way toward the distal extremity 84 of transparent guide piece body 82; as shown in the FIGS., bore 90 may pass all the way to, and may have an opening 95 on, the distal extremity 84.

As is disclosed in detail in copending U.S. patent application Ser. No. 08/833,984 filed Apr. 11, 1997, (A-64374), for example, an irrigation liquid such as saline may be conducted from a fitting 71 through the sheath 36 to exit through the transparent tip or guide piece 51 to clear the surroundings of the distal extremity of the device while in use within the body. The irrigation liquid can be conducted through the transparent guide piece by way of a thin gap between the outer surface of the distal extremity 80 of the optical viewing device 66 and the inner surface 91 of the longitudinal bore 90. Where the outside diameter of the distal extremity 80 of the optical viewing device is about 0.100 inches, for example, the inside diameter of the longitudinal bore 90 can be about 0.136 inches.

Transparent guide piece body 82 additionally is provided with a pair of channels 100, 101, which have openings 104, 105; at the proximal end 95 of guide piece body 82b; and openings 102, 103 at a surface of the guide piece 51 toward the distal extremity 84. These channels receive stylet guide tubes 106, 107. The lumens of the guide tubes 106, 107 commnunicate with the passageway 94 in elongate sheath 36, and are dimensioned such that stylet assemblies 46, 47 are slidably movable from behind through them and out through openings 102, 103. The channels and the stylet guide tubes within them are shaped so that they direct the stylet assemblies 46, 47 at a desired angle off-axis into the surrounding tissue.

While the channels 100, 101 may by themselves serve to guide the movement of the stylet assemblies 46, 47, the guide tubes 106, 107 can provide a superior internal surface for that purpose. The outer diameter of each stylet assembly can be slightly smaller than the inside diameter of the guide tubes, to provide unobstructed sliding movement of the stylet assemblies. Where the outside diameter of the stylet assembly is about 0.043 inches, for example, the inside diameter of the guide tubes can be about 0.058 inches.

As will be appreciated, the quality of the image of the surroundings of the guide piece, viewable by the optical viewing apparatus through the transparent guide piece material, depends upon the shape of the guide piece (particularly, the angles of incidence of light at the surface interface) and the optical qualities of the material from which the guide piece is made (particularly, the luminous transmittance and the index of refraction of the material).

The transparent guide piece body is made of a material having a high luminous transmittance, to provide both for good illumination and a relatively unobscured image within the field of view of the optical viewing device. Usually, the luminous transmittance of the guide piece body material is greater than about 80%, as determined in a specimen 0.3 mm thick using ASTM D 1003 procedures. Clearer images can be provided where the luminous transmittance of the guide piece body material is greater than about 80%, still clearer where it is greater than about 90%. Materials having sufficiently high luminous transmittance include transparent polymers, such as acrylate polymers (including polymethylmethacrylate), cellulose acetates, polycarbonates, polyurethanes, and polyethyleneterephthalates; and glasses.

The outer surface of the transparent guide piece presents an interface between the guide piece body material and the external milieu. To reduce lens effects as well as internal reflection effects at the surface interface, the guide piece body can be constructed of a material having an index of refraction approximating that of the external milieu. The fluids in the urethra, for example, which surround the distal extremity of a transurethral catheter device, have a refractive index approximately 1.33. Internal reflection and lens effects at the external surface of the transparent guide piece can be minimized by making the guide piece of a transparent material having a refractive index as near to 1.33 as practicable. Transparent materials useful in such a milieu include transparent polymers (which can have refractive indices in the range about 1.3 to about 1.7), such as acrylate polymers (for example polymethylmethacrylate), cellulose acetates, polycarbonates, polyurethanes, and polyethyleneterephthalates; and glasses.

To the extent that the refractive index of the transparent guide piece material is not matched to that of the surrounding milieu, some degree of internal reflection at the interface can be expected. As a matter of general optical principle, the degree of internal reflection depends upon the extent of the mismatch and upon the angle of incidence of the light, both of which can be readily determined for any material and any light path. Accordingly, a preferred shape for the transparent guide piece is one in which the extent of undesired internal reflection is minimized.

The transparent guide piece may be made by any of a variety of techniques, known in the art, including molding and casting and machining and combinations of molding and casting and machining. Most conveniently for example, the guide tubes can be shaped and positioned within a mold, and the transparent guide piece material can then be cast or molded around the guide tubes. The bore for the optical viewing device can either be molded or cast, or drilled after the guide piece body has hardened.

With further reference to FIGS. 2, 3 and 4, the operation and use of an insertable elongate medical device having a transparent guide piece according to the invention may now be briefly described as follows.

Let it be assumed that the apparatus has been prepared for carrying out a tissue ablation for treatment of a benign prostatic hypertrophy. Accordingly, light energy is being supplied to the fitting 69. Liquid is being supplied to the fitting 71 and a vacuum has been placed in communication with the port 73. Let it be assumed further that there has been appropriate preparation of the patient for the procedure. The probe 61 is then introduced by way of the penis into the urethra of the patient. As the probe is advanced through the urethra, the progress of the distal extremity can be directly observed through the eyepiece 67, and the progress is continued until the transparent guide piece 51 is appropriately located in the region of the prostate to be treated, which surrounds the urethra. This viewing is accomplished by having the optical viewing device 66 in its forward most position, as shown for example at 81a in FIG. 2, so that the image the operator sees at the eyepiece 67 is provided by the field of view outlined at 83a, distal to the extremity 84 of the transparent guide piece 51. Once the appropriate location at the prostate has been reached, the optical viewing device 66 can be retracted slightly (10 mm may be a suitable retraction distance) so it is in a more proximal position, indicated for example at 81b in FIG. 2. In this position the image the operator sees at the eyepiece 67 is provided by the field of view outlined at 83b, just proximal to the distal extremity of the guide piece, and proximal to the openings 102, 103 so that deployment of the needle assemblies 46 and 47 can be observed. This deployment is accomplished by appropriate positioning of the sliders 58 and 61 to cause the distal extremities of the needle electrodes 46 and 47 to project sidewardly or off axis through the urethral wall and into the selected lobe of the prostate to be treated. As soon as the needle electrode assemblies 46 and 47 have been advanced as far as desired into the prostate, the sliders 59 and 62 can be moved to cause retraction of the sleeves 53 surrounding the electrodes 52 to expose predetermined lengths of the electrodes within the prostatic tissue while still retaining the insulating sleeves so that they extend 'slightly beyond the urethral wall so as to protect the urethral wall from radio frequency ablation.

Then the electrical energy can be applied to disrupt the tissue within the prostate lobe without risk of exposing and causing trauma to surrounding tissues. Once the needle ablation has been completed, sliders 58 and 61 and 59 and 62 can be moved as appropriate to retract the needle assemblies 46 and 47 back into the guide tubes 106, 107 within the guide piece 51. Device 16 is then withdrawn from the urethra.

Figure 5:
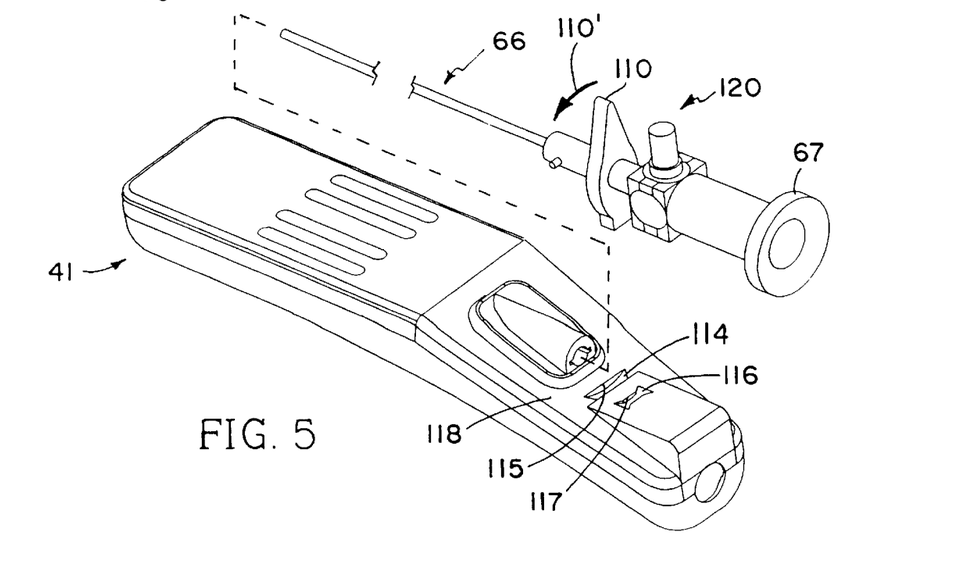
FIG. 5 is a sketch in an exploded view of the handle means and proximal extremity of the optical viewing device, showing means according to the invention for locking the longitudinal position of the optical viewing apparatus.

FIG. 5 shows a simple locking mechanism in the handle 41, for readily ensuring that the distal extremity of the optical viewing device is held securely in the first or second positions.

FIG. 5 shows an exploded view of portions of the handle 41 and the proximal extremity 120 of the optical viewing device 66. Locking lever 110 is rotatable about the longitudinal axis of the optical viewing apparatus, and has a am portion 112 engageable with one of a pair of detents 114, 116 in the subjacent upper surface 118 of handle 41. For example, to lock the optical viewing apparatus in the more distal position, the optical viewing device 66 is slid distally until the cam portion 112 is aligned with the more distal detent 114 and then the lever 110 is rotated (for example as shown by arrow 110") so that the cam 112 engages detent 114. The optical viewing apparatus may be withdrawn to the more proximal position, by rotating lever 110 to disengage cam 112 from detent 114 and sliding the optical viewing apparatus in a proximal direction until the locking mechanism is aligned with detent 116, and then rotating the lever 110 so that cam 112 engages detent 116. When the optical viewing apparatus is in this position, its distal extremity is in a correspondingly more posterior position, as for example 81b) in FIG. 2, so that the image carried to the eyepiece 67 is provided by the field of view shown in outline at 83b in FIG. 2.

The distance between the forward edges 115, 117 of detents 114, 116 establishes the longitudinal displacement of the distal extremity of the optical viewing apparatus which may be, for example, about 10 mm.

As will be appreciated, the invention as described above provides for viewing simultaneously both in a direction distal to the distal extremity of the guide piece, and in a direction (through the transparent body of the guide piece) lateral to the distal extremity of the guide piece, when the distal extremity of the optical viewing apparatus is in a more proximal position.

Further, as noted above, some degree of internal reflection can be expected to occur at the interface at the surface of the guide piece body, owing to the fact that there is a refractive index mismatch between the guide piece body material and the fluids surrounding the guide piece. And, as noted above, to the extent that internal reflection may be undesirable, for example because it may produce a glare that interferes with image quality, the guide piece body material may be selected to minimize the refi-active index mismatch, and the shape of the guide piece surface may be designed so to avoid unwanted internal reflection.

However, we have discovered that the internal reflection property of the material can be exploited to provide a split image, viewable at the eyepiece. Such a split image consists in part of a distal view, and in part of a lateral view, principally to one side of the longitudinal axis of the optical viewing apparatus. This is accomplished by providing the distal extremity of the transparent guidepiece with a planar face, inclined at an oblique angle with respect to the longitudinal axis of the optical viewing apparatus. As a result of this configuration, some light, coming from points normally laterally outside the field of view of the optical viewing device, is reflected toward the optical viewing device from the inner side of the interface formed by the planar face, while some other light coming from points normally within the field of view of the optical viewing device, are reflected or refracted at the interface such that they do not reach the optical viewing device.

Figures 6, 7:
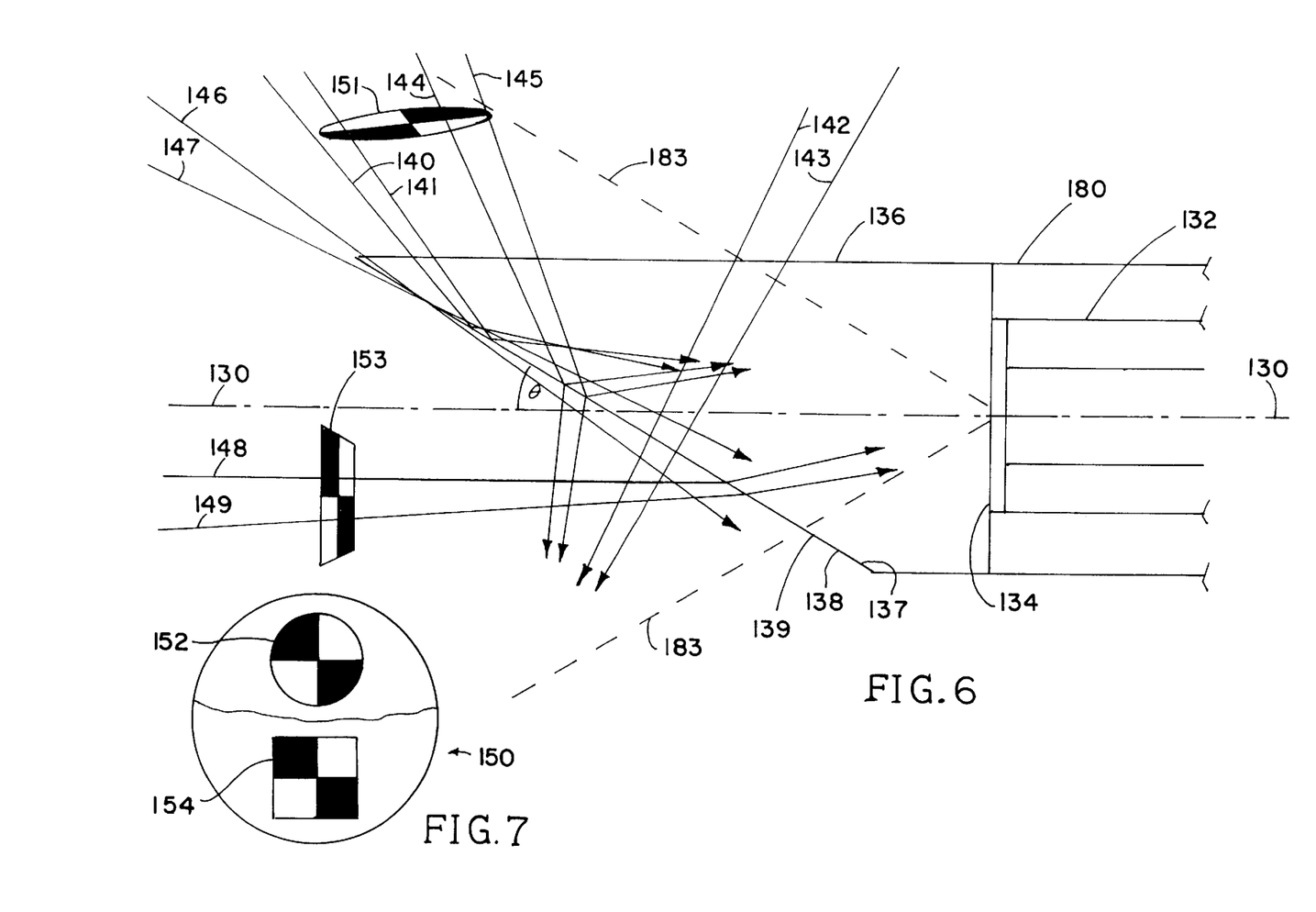
FIG. 6 is a sketch in a side elevational view of a transparent distal extremity capable in cooperation with an optical viewing device of producing a split image, according to the invention.
FIG. 7 is a sketch showing a split image hypothetically formed using the transparent distal extremity as in FIG. 6.

This effect has been proven in principle using a device shown in FIG. 6. There is shown a rod lens element 132 having a distal face 134, which in the example shown is perpendicular to the longitudinal axis 130 of the optical viewing device, and a transparent tip 136 having a generally circular cross section about the longitudinal axis 130 and a planar face 138 that is inclined at an oblique angle $\theta$ with respect to the longitudinal axis 130. The planar face 138 provides an interface having an inner side 137 and an outer side 139. Transparent tip 136 is constructed of a material having a refractive index greater than that of the fluid in the milieu (adjacent the outer side 139) that bathes the face 138. As a result of the refractive index mismatch at the planar face, internal reflection effects cause internal reflection of certain of the light rays that are incident on the inner side 137 of the interface. Particularly, as a matter of general optical principle, light rays that meet the inner side 137 at an angle of incidence less than the critical angle are reflected in a proximal direction, and some of these are directed toward the face 134 of rod lens element 132 (for example, rays 140, 141); while rays that meet the inner side 137 at an angle of incidence greater than the critical angle either pass through the interface (for example, rays 142, 143) or pass through in part and are reflected in part (for example, rays 144, 145). As a consequence, the effective field of view toward one side of the longitudinal axis 130 (that is, toward the inner side 137 of the interface provided by the face 138) is substantially widened beyond the peripheral limit 183 provided by the rod lens itself, so that the image toward that side of the device includes at its margin (Treater portions of the surroundings Light rays that are traveling parallel or approximately parallel to the face 138 on either side of the interface (for example, rays 146, 147) are not directed toward the face 134 of the rod lens element, and do not form part of the image.

Light rays that are incident upon the outer side 139 of the interface, that is, light rays coming from more distal directions and from lateral directions toward the opposite side of the longitudinal axis 130, are either reflected or are refracted at the interface; some of these rays (for example, rays 148, 149) reach the face 134 of the rod lens element.

As will be readily appreciated from the foregoing description, the shape of the resulting image depends upon the angle $\theta$, and the refractive indices of the external milieu and of the material from which the tip 136 is made.

Transparent tip 136 may be formed of any suitably transparent material having an index of refraction higher than that of the external milieu. Suitable transparent materials include, for example, transparent polymers. A polycarbonate having a refractive index about 1.58 may be particularly suitable for a tip having a face 138 inclined at an oblique angle $\theta$ of about 30°. A sketch of a hypothetical image resulting from a tip made of such a polycarbonate in such a configuration and conducted by a rod lens element to an eyepiece is shown in FIG. 7. The generally circular image 150 includes a lateral image portion 152 of a hypothetical object 151 and a distal image portion 154 of a hypothetical object 153.

The angle $\theta$ will be determined on the basis of general optical principles, taking account of the respective indices of refraction of the material of which the tip is made and of the surrounding fluid (which may, for example, be saline), and in view of the positions of the objects that it is desired to bring into the image. Preferably, the plane is inclined to the optical axis of the optical viewing device at an angle less than or equal to the critical angle, which may be readily calculated for any combination of materials.

As will be appreciated, portions of the tip 136 other then the face 138 can be shaped other than as shown in FIG. 6. In particular, a transparent guide piece 51 as shown for example in FIGS. 2–4 can be formed to exploit the principle demonstrated by the operation of tip 136, by providing the transparent guide piece 51 with a planar distal surface inclined at an oblique angle with respect to tile longitudinal axis of the distal extremity. Such a guide piece could operate substantially as described above with reference to FIGS., 2–4 and, additionally, could provide for silmiltaneous split viewing Where a transparent guide piece is so shaped to provide a split view, the distal extremity of the optical viewing device need not necessarily be moved longitudinally in order to provide the desired range of lateral and distal views and, accordingly, the transparent guide piece need not necessarily be provided with a longitudinal bore.

It is apparent from the foregoing that the invention provides medical probe devices that have a capability for excellent viewing both during placement of the device at the treatment site and during the progress of the treatment. Where the device is a transurethral catheter for treatment of the prostate, the invention enables precise location of the device at the site, and for visual monitoring of the deployment of the treatment means, to ensure that the treatment will be effective in the target tissues, and will not damage surrounding tissues.

Other embodiments are within the claims. For example, the invention includes devices that are introduced into the body by other routes than the urethra, and devices that are intended for treatment of tissues or organs other than the prostate. And, for example, the invention includes devices useful for observation of particular sites within the body, whether or not used for treatment as well. And, for example, the invention includes devices in which the treatment means employs application of energy other than electrical energy for ablation of tissue, and in which the treatment means effects removal or reduction of tissues other than by application of energy to the target tissue.

What is claimed is:

1. A medical probe device for treatment of a prostate of a human male having a bladder with a base with a urethra formed by a urethral wall extending into the base of the bladder with the tissue of the prostate surrounding the urethra near the base of the bladder comprising an elongate probe member having proximal and distal extremities and a longitudinal axis and a passageway extending from the proximal extremity to the distal extremity along the longitudinal axis, the elongate probe member having a length so that when the distal extremity is disposed in the urethra in the vicinity of the prostate the proximal extremity is outside the urethra, handle means coupled to the proximal extremity of the elongate probe member for introducing the distal extremity of the elongate probe member into the urethra, a stylet slidably mounted in the passageway of the elongate probe member, a guide piece mounted on the distal extremity of the elongate probe member, the guide piece having a proximal extremity and a rounded distal end and an internal curved surface for directing the stylet sidewise of the longitudinal axis into the tissue of the prostate, an optical viewing device mounted within the passageway of the elongate probe member and having a distal extremity with a field of view positionable in the vicinity of the guide piece, the guide piece being made from a transparent material to permit viewing by the distal extremity of the optical view device forwardly and sidewardly of the guide piece.

2. The medical probe device of claim 1 wherein the stylet includes a conductive radio frequency electrode and a layer of insulating material disposed around the conductive radio frequency electrode but exposing a distal portion of the conductive radio frequency electrode.

3. The medical probe device of claim 1 further comprising means carried by the handle means for moving the distal extremity of the optical viewing device between forward and rearward positions within the guide piece.

4. The medical probe device of claim 1 wherein the transparent material is a transparent polymer.

5. A medical probe device for introduction by way of a natural body opening into an internal cavity of a body to a treatment site comprising an elongate probe member having proximal and distal extremities and a longitudinal axis and a passageway extending from the proximal extremity to the distal extremity along the longitudinal axis, handle means coupled to the proximal extremity of the elongate probe member for introducing the distal extremity of the elongate probe member into the natural body opening, a stylet slidably mounted in the passageway of the elongate probe member, a guide piece mounted on the distal extremity of the elongate probe member, the guide piece having a proximal extremity and a rounded distal end and an internal curved surface for directing the stylet sidewise of the longitudinal axis into tissue at the treatment site, an optical viewing device mounted within the passageway of the elongate probe member and having a distal extremity with a field of view positionable in the vicinity of the guide piece, the guide piece being made from a transparent material to permit viewing by the distal extremity of the optical view device forwardly and sidewardly of the guide piece.

6. The medical probe device of claim 5 wherein the stylet includes a conductive radio frequency electrode and a layer of insulating material disposed around the conductive radio frequency electrode but exposing a distal portion of the conductive radio frequency electrode.

7. The medical probe device of claim 5 further comprising means carried by the handle means for moving the distal extremity of the optical viewing device between forward and rearward positions within the guide piece.

8. The medical probe device of claim 5 wherein the transparent material is a transparent polymer.

* * * * *